(12) United States Patent
Nutting

(10) Patent No.: US 8,517,733 B1
(45) Date of Patent: Aug. 27, 2013

(54) REMOVABLE TOOTH CAP AND METHOD OF ATTACHMENT THEREFOR

(75) Inventor: Donald W. Nutting, Boulder, CO (US)

(73) Assignee: Foothills Creations Ltd, Boulder, CO (US)

( * ) Notice: Subject to any disclaimer, the term of this patent is extended or adjusted under 35 U.S.C. 154(b) by 1152 days.

(21) Appl. No.: 11/366,902

(22) Filed: Mar. 1, 2006

Related U.S. Application Data

(60) Provisional application No. 60/658,747, filed on Mar. 3, 2005.

(51) Int. Cl.
*A61C 13/225* (2006.01)

(52) U.S. Cl.
USPC .......................................................... 433/183

(58) Field of Classification Search
USPC ................... 433/180–183, 218–221; 472/70, 472/133
See application file for complete search history.

(56) References Cited

U.S. PATENT DOCUMENTS

| | | | |
|---|---|---|---|
| 723,102 A * | 3/1903 | Whiteside | 433/220 |
| 758,750 A * | 5/1904 | Haldeman | 433/221 |
| 1,379,063 A | 5/1921 | Van Allen | |
| 1,423,027 A * | 7/1922 | Rose | 433/218 |
| 2,057,341 A | 10/1936 | Morgan | |
| 2,799,933 A * | 7/1957 | Neustadter | 433/183 |
| 3,558,540 A | 1/1971 | Molnar | |
| 3,793,728 A | 2/1974 | Corbineau | |
| 4,015,332 A | 4/1977 | Manne | |
| 4,206,545 A | 6/1980 | Lord | |
| 4,251,215 A | 2/1981 | May et al. | |
| 4,430,061 A | 2/1984 | Webb et al. | |
| 4,678,435 A | 7/1987 | Long | |
| 4,738,622 A | 4/1988 | Kawahara et al. | |
| 5,102,337 A | 4/1992 | Soroca | |
| 5,324,198 A | 6/1994 | Hazen | |
| 5,403,186 A | 4/1995 | Ginsburg | |
| 5,547,381 A | 8/1996 | Nutting | |
| 5,569,036 A | 10/1996 | Goldiner et al. | |
| 5,951,294 A * | 9/1999 | Pierson | 433/218 |
| D447,240 S * | 8/2001 | Walker, Sr. | D24/156 |

FOREIGN PATENT DOCUMENTS

WO 9103210 3/1991

OTHER PUBLICATIONS

Generik Ink, Inc. Why Not Party? Horror Film Make-Up instruction sheet, 1988.
Fangtastics fang instruction sheet (date unknown-admitted prior art).
Scarecrow Custom Fangs instruction sheet (date unknown-admitted prior art).

(Continued)

*Primary Examiner* — Cris L Rodriguez
*Assistant Examiner* — Hao D Mai
(74) *Attorney, Agent, or Firm* — Brian D. Smith, P.C.

(57) ABSTRACT

A generally hollow removable tooth cap defines a cavity for receiving a real tooth as well as material for removably attaching the tooth cap to the real tooth. The tooth cap has a front side and a back side which terminate together at the distal or free end of the tooth cap. The back side of the tooth cap further defines a recessed area which extends longitudinally along the backside from an area adjacent the distal end of the tooth cap until it opens into the cavity of the tooth cap. The tooth cap is also provided with a nonlinear passageway in the bottom of the tooth cap's cavity for receiving the attaching material to secure the material to the tooth cap.

18 Claims, 3 Drawing Sheets

(56) References Cited

OTHER PUBLICATIONS

262 Cheap Scarecrow Fang photographs (date unknown-admitted prior art).
373 Original Fangtastics Fang photographs (date unknown-admitted prior art).
449 New Fangtastics Fang photographs (date unknown-admitted prior art).
386 Professional Fangtastics Fang photographs (date unknown-admitted prior art).
410 New Bloody Mary Fang photographs (date unknown-admitted prior art).
224 Norben Fang photographs (date unknown-admitted prior art).
421 Hot Topic Fang photographs (date unknown-admitted prior art).
433 Fun World Fang photographs (date unknown-admitted prior art).
324 Old Foothills design Fang photographs (date unknown-admitted prior art).
Fun World Tooth Cap drawing drawn by inventor Donald Nutting (date unknown-admitted prior art).

* cited by examiner

REMOVABLE TOOTH CAP AND METHOD OF ATTACHMENT THEREFOR

CROSS REFERENCE TO RELATED APPLICATION

This application is a nonprovisional application claiming the benefit under 35 USC 119(e) of U.S. provisional application No. 60/658,747, filed on Mar. 3, 2005.

FIELD OF THE INVENTION

The invention relates generally to removable tooth caps and more particularly to removable tooth caps providing a realistic appearance and a comfortable fit.

BACKGROUND OF THE INVENTION

In the course of parties, particularly Halloween parties, it is common to have people masquerade as vampires and other wild beasts. In doing so, these people are faced the problem of using tooth caps that simulate fangs.

The first company to produce preformed universal tooth cap bodies was Violet's with their Fangtastics brand of fangs. Scarecrow followed with their individual tooth caps commonly known as Scarecrow Fangs. Thirdly, Foothills LTD followed with their Custom Dracula Fangs. Other fangs that followed appear to imitate in one form or another of these three tooth cap bodies.

The Fangtastics design of a tooth cap body, with its shallow cavity trough for tooth insertion, was unstable, and the fangs had a tendency to fall out. The Scarecrow Fangs design has a deep cavity trough which attempts to provide adequate tooth support, but lacks a comfortable fit with a good bite. Foothills LTD's Custom Dracula Fangs design also has a deep enough cavity trough providing good tooth support, and a comfortable fit with a good bite; but at times the wearer, while making a partial plate during the thermoplastic fang application, can push the fang forward (when biting down to achieve a natural bite) because of the thermoplastic still being soft; thus causing the appearance of the fang to not be as realistic.

SUMMARY OF THE INVENTION

A major object of the present invention is to provide a custom fit tooth cap that has a more comfortable fit and a better bite for the wearer, while not interfering with the placement or mounting of the tooth cap on the wearer's real tooth so as to not detract from the realistic appearance provided by the tooth cap or interfere with the user's normal occlusion when the tooth cap is attached to the user's real tooth.

Another object of the present invention is to enhance attachment of the material used to attach the tooth cap to the real tooth to the tooth cap.

Yet another general object of the present invention is to provide an inexpensive tooth cap that attaches to a real tooth without any need for specialized equipment or specialized training.

Additional objects, advantages, and novel features of the present invention shall be set forth in part in the description that follows, and in part will become apparent to these skilled in the art upon examination or may be learned by the practice of the invention. The objects and the advantages may be realized and attained by means of the instrumentalities and in combinations particularly pointed out in the appended claims.

To achieve the forgoing and other objects and in accordance with the purposes of the present invention, as embodied and broadly described herein, the present invention provides a generally hollow removable tooth cap which defines a cavity (sometimes referred to as a first chamber) for receiving a real tooth as well as material for removably attaching the tooth cap to the real tooth. The tooth cap has a front side and a back side with the back side being shaped so as to minimize contact with opposing teeth when the teeth of the upper and lower jaws are brought together in their normal occlusion.

In a preferred embodiment, the tooth cap's back side defines a preferably concave shaped recessed area which extends longitudinally along the back side of the tooth cap from an area adjacent the free or distal end of said tooth cap. The back side and recessed area terminate at an edge or lip near the mid-section of the tooth cap so that the recessed area opens into the cavity of the tooth cap. As such, an opposing tooth of the wearer can ride or be received in the recessed area and the cavity of the tooth cap when the wearer bites down with the tooth cap. In addition, by providing this recessed area or path for the wearer's opposing tooth, pushing forward of the tooth cap on the wearer's real tooth is prevented or at least minimized, thereby insuring a realistic appearance of the tooth cap when fit on the wearer's real tooth. Moreover, all of this is accomplished without significantly interfering with the wearer's normal occlusion.

To further insure that the tooth cap does not interfere with the wearer's normal occlusion and yet provide sufficient side support from back side 22, another preferred embodiment of the present invention cuts back or slopes the back edge of the tooth cap's back side so that the back edge forms an included angle of between about 100 and 130 degrees with peripheral rim of the tooth cap's front side.

In yet another preferred embodiment of the invention, the tooth cap defines a nonlinear passageway (sometimes referred to as a second chamber) in the bottom of the tooth cap's cavity for receiving attaching material to secure the attaching material to the tooth cap. The nonlinear passageway provides an extremely strong bond between the tooth cap and the attaching material when the passageway is filled or at least partially filled with the attaching material and the material hardens or cures. In fact, the resulting bond is usually so strong that it can be considered to lock the attaching material to the tooth cap.

BRIEF DESCRIPTION OF THE DRAWINGS

The accompanying drawings, which are incorporated in and form a part of the specification, illustrate the preferred embodiments of the present invention, and together with the descriptions serve to explain the principles of the invention. In the Drawings.

DETAILED DESCRIPTION OF THE PREFERRED EMBODIMENTS

Figure 7:
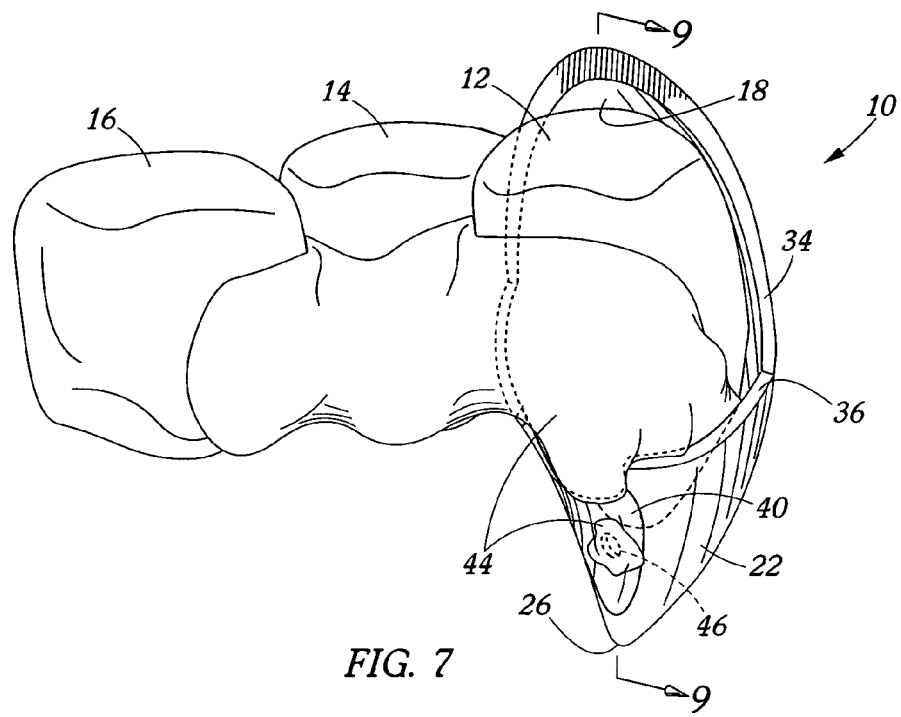
FIG. 7 is a perspective view showing the tooth cap of FIG. 1 mounted on the left upper canine tooth and anchored to the first and second upper left premolars looking from the inside of a wearer's mouth to the outside. The tooth cap is positioned on the canine tooth and a portion of thermoplastic material extends from the cavity inside the tooth cap to the first and second premolars.

Turning now to the drawings, FIGS. 1 through 6 illustrate the tooth cap 10 of the present invention in isolation. FIG. 7 shows tooth cap 10 mounted or positioned on an individual's left upper canine tooth 12. While shown on a canine tooth, the tooth cap could be mounted on any other canine tooth, an incisor tooth, or any other tooth capable of being received in the cavity 18 of the tooth cap. As also shown, tooth cap 10 includes a generally convex shaped front side 20 and back side 22 which converge together to form an extension 24, a tip 26, and a trough 28 of the tooth cap's cavity 18. As perhaps best shown in FIG. 8, cavity 18 is defined by generally concave shaped inside surfaces 30, 32 of the tooth cap's front and back sides 20, 22, respectively. As also shown, the concave shaped inside surface 30 of front side 20 terminates at a generally flat peripheral edge or rim 34 while the inside surface 32 of the back side 22 terminates at an edge 36 referred to as back edge 36 which abuts rim 34. As further shown, back edge 36 is generally flat except along its central section which is referred to herein as the central arcuate cutout edge 38.

Figure 3:
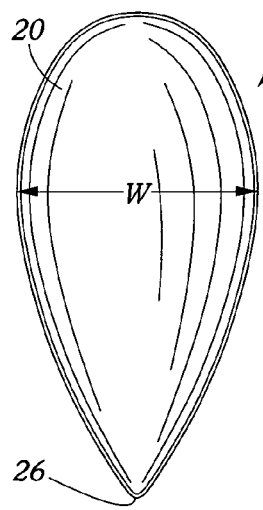
FIG. 3 is a front elevational view of the tooth cap of FIG. 1.
Figure 4:
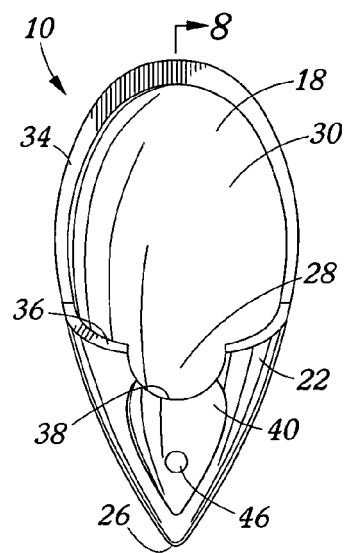
FIG. 4 is a rear elevational view of the tooth cap of FIG. 1.
Figure 5:
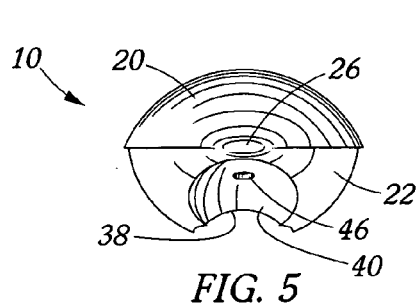
FIG. 5 is a bottom plan view of the tooth cap of FIG. 1.
Figure 6:
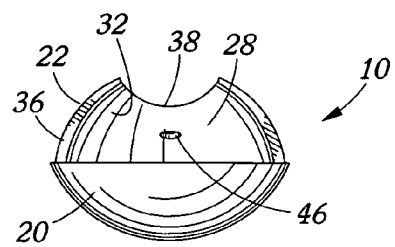
FIG. 6 is a top plan view of the tooth cap of FIG. 1.

As shown in FIG. 3, tooth cap 10 is provided with an appropriate width W, size, and shape to conform to the lateral side of real tooth 12 so that when the tooth cap is placed on the real tooth, the tooth cap becomes a realistic and natural appearing extension of the real tooth. The outside surface (not numbered) of front side 20 has a convex shape to further accentuate the realistic visual effect of the tooth cap for the masquerader, as well as provide sufficient thickness to accommodate the cavity 18 extending therein from the inside, as described above and shown in FIGS. 4 and 8.

Figures 8, 9, 10:
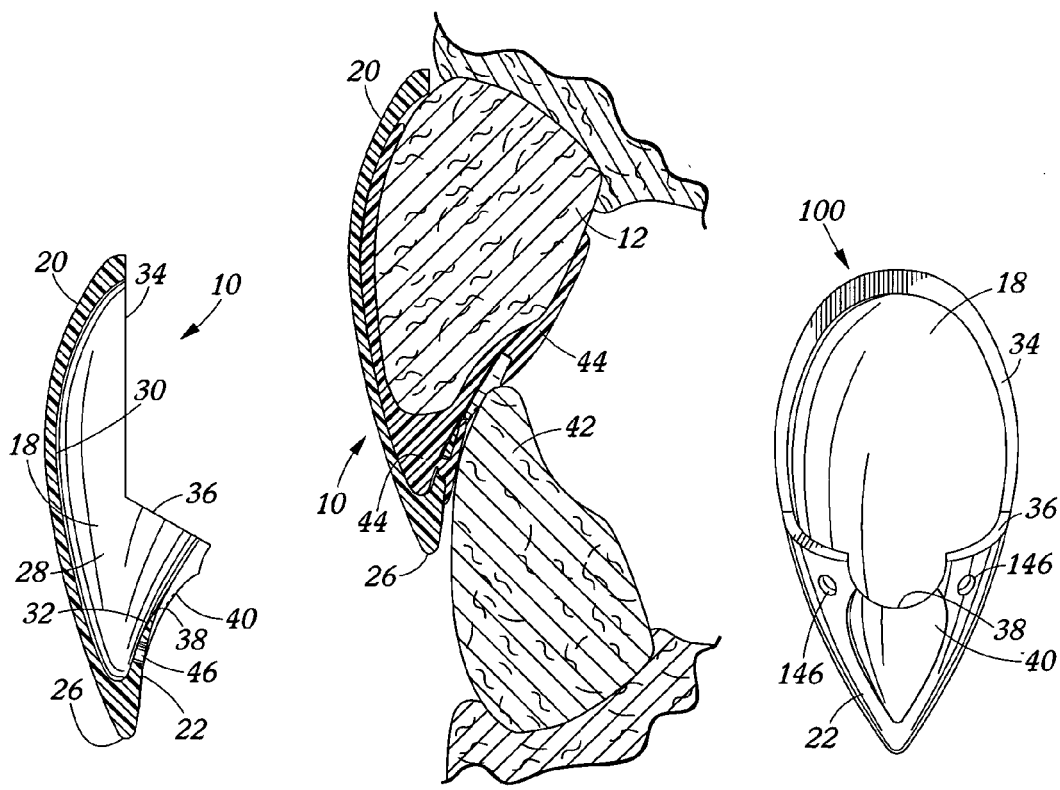
FIG. 8 is a cross sectional view taken along lines 8-8 of FIG. 4.
FIG. 9 is a cross sectional view similar to FIG. 8 which additionally shows the tooth cap of FIG. 1 mounted on and attached to a user's real tooth as well as an opposing tooth of the user received in the recessed area of the tooth cap.
FIG. 10 is a rear elevational view of a tooth cap which is identical to that of FIG. 1 except that the tooth cap of FIG. 10 is provided with a pair of holes 146 instead of the single hole 46 provided in the tooth cap of FIG. 1.

When tooth cap 10 is worn by the masquerader (also referred to as the wearer or user herein) the extremity edge of the real tooth is preferably positioned in the cavity trough 28 as shown in FIGS. 7, 8 which restricts or eliminates lateral motion of the tooth cap relative to the real tooth, especially when material for attaching the tooth cap to the real tooth is introduced into the cavity trough as described in more detail below.

In addition, as shown in FIGS. 4-6 and 8, the tooth cap's generally convex shaped back side 22 defines a concave shaped recessed area 40 which extends longitudinally along the back side of the tooth cap from an area adjacent the tip 26 (free distal end) of the tooth cap. As also shown, the back side 22 and recessed area 40 terminate at back edge 36 and central cutout edge 38, respectively, near the mid-section of the tooth cap so that the recessed area 40 opens into cavity 18 (more specifically cavity trough 28) of the tooth cap. As such, an opposing tooth 42 of the wearer can ride or be received in the recessed area 40 and the cavity of the tooth cap when the wearer bites down with the tooth cap, as shown in FIG. 9.

In addition, by providing this recessed area 40 or path for the wearer's opposing tooth, pushing forward of the tooth cap on the wearer's real tooth is prevented or at least minimized, thereby insuring a realistic appearance of the tooth cap when fit on the wearer's real tooth. Moreover, all of this is accomplished without significantly interfering with the wearer's normal occlusion.

Figure 1:
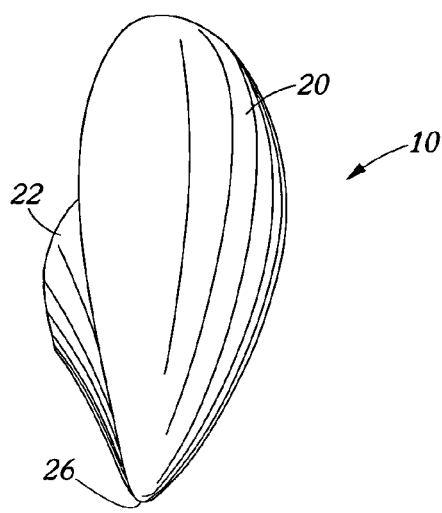
FIG. 1 is a perspective view of the tooth cap of the present invention.
Figure 2:
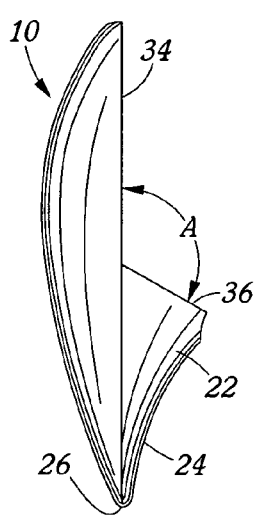
FIG. 2 is a side elevational view of the tooth cap of FIG. 1 which shows the angle A or slope of the back edge of the tooth cap's back side.

To further insure that the tooth cap does not interfere with the wearer's normal occlusion and yet provide sufficient side support from back side 22, back edge 36 is cut back (relative to the corresponding back edge of the tooth cap shown in my previously issued U.S. Pat. No. 5,547,381 which is incorporated herein by reference) so that back edge 36 forms an included angle A of about 120 degrees with peripheral rim 34, as shown in FIG. 2. While a 120 degree included angle is shown, good results should be obtainable with an included angle greater than about 100 degrees with preferred results expected between 100 and 130 degrees.

A preferred method for attaching tooth cap 10 of the present invention to a real tooth is described in my U.S. Pat. No. 5,547,381. As generally described therein, a quantity of thermoplastic material (shown herein in FIG. 9 as thermoplastic 44) is placed in cavity 18 and cavity trough 28 after it has been heated and is thereby in a flowable state. The tooth cap with flowable thermoplastic material contained therein is then placed on the real tooth and the excess thermoplastic is spread by the user over the adjacent teeth 14, 16 (or other adjacent teeth, not shown) to make a partial plate for the wearer which comprises the tooth cap and the thermoplastic and which securely attaches the tooth cap to the user's teeth when the thermoplastic hardens but which also enables the tooth cap to be easily removed from the user's teeth due to the resiliency of the hardened thermoplastic which allows the partial plate to be easily removed from the teeth even though the thermoplastic has hardened. As also shown in FIG. 7, attachment of the thermoplastic material to the tooth cap 10 is enhanced by providing the tooth cap with a hole 46 which allows the flowable thermoplastic to flow through the hole and onto the surface of recessed area 40. When the thermoplastic material hardens as also described in my U.S. Pat. No. 5,547,381, the tooth cap will be securely attached to the hardened thermoplastic. As also shown in FIG. 7, thermoplastic material also flows over cutout edge 38 onto the recessed area which further enhances attachment of the thermoplastic to the tooth cap when it hardens.

FIG. 10 shows another tooth cap 100 of the present invention which is identical to tooth cap 10 except that tooth cap 100 is provided with a pair of holes 146 instead of a single hole 46. The use of two holes instead of one is expected to provide better attachment or anchoring of the thermoplastic material to the tooth cap.

Figure 11:
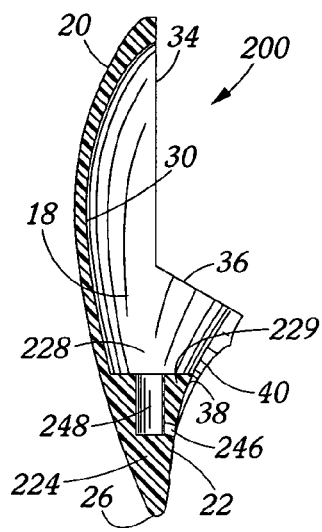
FIG. 11 is a cross sectional view of another embodiment of the present invention which is similar to the view of FIG. 8.
Figure 12:
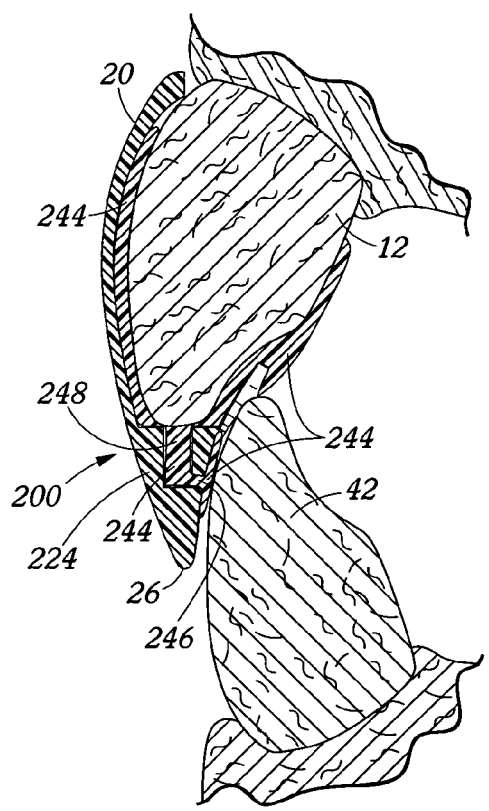
FIG. 12 is another cross sectional view of the embodiment of FIG. 11 which is similar to the view of FIG. 9.

FIGS. 11 and 12 illustrate yet another tooth cap 200 of the present invention which is similar to tooth cap 10 and utilizes the same reference numerals to identify features which are the same in both embodiments. While similar, it will be appreciated that the cavity trough 228 of tooth cap 200 is shallower than trough 28 of tooth cap 10. As such, the bottom surface 229 of trough 228 is raised relative to that of tooth cap 10. In addition, it will be appreciated that extension 224 of tooth cap 200 is provided with a cylindrically shaped passageway 248 which extends through and from bottom surface 229 to another cylindrically shaped passageway 246 which extends through the outer surface (not numbered) of the tooth cap's backside 22. As shown, passageways 246 and 248 are in fluid communication with each other and thereby allow flowable thermoplastic 244 which is placed in cavity trough 228 to flow through passageways 248, 246 to the outside surface of the tooth cap's extension, as shown in FIG. 12. When the thermoplastic cools and hardens as shown in FIG. 12 about the wearer's tooth 12, in the bottom of the trough 228, in passageways 246, 248 and on the outer surface of the backside of the tooth cap, an extremely strong mechanical bond (anchoring) between the thermoplastic and the tooth cap 200 is provided, thereby insuring that the thermoplastic will remain securely attached to the tooth cap and as such enable the user to reuse the tooth cap for years if desired. While this embodiment shows two passageways adjoining each other at an angle so as to make a bend, any nonlinear passageway capable of receiving flowable thermoplastic or a similar material should form an extremely strong mechanical bond between the material and the tooth cap, essentially locking the material to the tooth cap. In fact, it is not even necessary that the passageway extend through the outer surface of the tooth cap. However, by extending the passageway through the tooth cap's outer surface preferably the back side surface, air pocket formations in the passageway are less likely to occur. Air pockets in the passageway are undesirable because they can prevent the material from flowing into the passageway and forming a strong bond between the material and the tooth cap.

While the illustrated embodiments are provided with holes 46 and 146 and passageways 246 and 248 for anchoring the thermoplastic to the illustrated tooth caps, other surface features such as ridges and depressions could also be employed to enhance attachment of the thermoplastic material to the tooth cap as described in my U.S. Pat. No. 5,547,381.

As indicated, thermoplastic is the preferred material for attaching the tooth cap of the present invention to a real tooth. However, other materials for attaching tooth cap 10 to a real tooth may also be used such as Sea Bond which was used in the application method for attaching the original Fangtastics fang. Other suitable attaching materials include Scarecrow's liner material, Coe-Soft, Scarecrow's newer A & B chemical material, which hardens like an epoxy, Fun World's fang putty, denture adhesive, or any flowable material which later hardens, partially or completely.

While my U.S. Pat. No. 5,547,381 describes a preferred method for attaching the tooth cap of the present invention to a real tooth, a method specifically tailored for applying the tooth cap of the present invention to a real tooth includes the following steps:

1. Providing a tooth cap 10 or similar tooth cap defining a cavity for receiving a real tooth wherein the surface of said cavity is provided with surface features for enhancing the attachment of material for removably attaching said tooth cap to the real tooth;

2. Placing material for removably attaching tooth cap 10 to a real tooth into the cavity of tooth cap 10;

3. Placing tooth cap 10 onto the real tooth so that the attaching material envelops the surface features; and then 4. Biting down to adjust the tooth cap's position on the real tooth so that interference caused by the tooth cap with the user's normal occlusion is minimized; and, 5. While biting down, allowing the attaching material to set so that the tooth cap is affixed to the real tooth in the position which minimizes said interference.

In the embodiment of FIGS. 11 and 12, the foregoing placing step 3 forces the attaching material down into the passageway 248 and out through passageway 246.

The foregoing description is considered as illustrative only of the principles of the invention. Furthermore, since numerous modifications and changes will readily occur to those skilled in the art, it is not desired to limit the invention to the exact construction and process shown and described above. Accordingly, all suitable modifications and equivalents that may be resorted to are considered to be within the scope of the invention as defined by the claims that follow. For example, while the recessed area 40 as shown in the figures has a bottom until it terminates at edge 38, it could be completely or partially bottomless along its entire longitudinal length on the back side 22 of the tooth cap, or it could terminate at a different location on the back side of the tooth cap.

What is claimed is:

1. A generally hollow removable and re-usable tooth cap of the type that is attachable to and removable from a user's real tooth by the user, said tooth cap defining a cavity for receiving a full-size real tooth as well as material for removably attaching said tooth cap to the full-size real tooth, said tooth cap having a front side and a backside which terminate at a distal end of said tooth cap, said cavity being defined by an inside surface of said front side and an inside surface of said backside, said backside of said tooth cap further defining a recessed path on its outer surface, said path extending longitudinally along said backside of said tooth cap from an area adjacent said distal end of said tooth cap to a back edge of said backside near a mid-section of the tooth cap at which said backside and said path terminate.

2. A tooth cap as claimed in claim 1 wherein said recessed path opens into said cavity of said tooth cap.

3. A tooth cap as claimed in claim 1 wherein said recessed path is bottomless at least along a portion of its length.

4. A tooth cap as claimed in claim 1 wherein said recessed path has a concave shape at least along a portion of its length.

5. A tooth cap as claimed in claim 1 wherein said front side and backside converge to a tip at the distal end of the tooth cap so that the tooth cap will look like a fang when attached to a person's real tooth.

6. A tooth cap as claimed in claim 1 wherein said cavity is provided with surface features for enhancing attachment of the attaching material to said tooth cap.

7. A tooth cap as claimed in claim 6 wherein said surface features include at least one hole extending from said cavity through said backside of said tooth cap.

8. A tooth cap as claimed in claim 6 wherein said surface features include at least one hole extending through said recessed path of said backside of said tooth cap.

9. A tooth cap as claimed in claim 6 wherein said cavity defines a cavity trough having a bottom surface and wherein said surface features include a passageway extending through and from said bottom surface to and through said backside of said tooth cap.

10. A tooth cap as claimed in claim 9 wherein said passageway includes a pair of passageways in fluid communication with each other.

11. A tooth cap as claimed in claim 9 wherein said passageway makes a bend as it extends from said bottom surface of said cavity trough to and through said backside of said tooth cap.

12. A tooth cap as claimed in claim 1 wherein said front side defines a peripheral rim and said backside defines a back edge and wherein said rim and back edge adjoin each other so as to form an included angle which is greater than about 100 degrees.

13. A tooth cap as claimed in claim 12 wherein said rim and back edge form an included angle ranging between about 100 and 130 degrees.

14. A tooth cap as claimed in claim 12 wherein said rim and back edge form an included angle of about 120 degrees.

15. A generally hollow removable and re-usable tooth cap of the type that is attachable to and removable from a user's real tooth by the user, said tooth cap defining a cavity for receiving a full-size real tooth as well as material for removably attaching said tooth cap to the full-size real tooth, said cavity having a bottom, and said tooth cap further defining a nonlinear passageway in said bottom of the tooth cap's cavity for receiving the material to secure the material to the tooth cap, said nonlinear passageway extending from said bottom of said cavity to and through the outer surface of said tooth cap.

16. A tooth cap as claimed in claim 15 wherein said tooth cap has a front side and a back side and wherein said cavity is defined by an inside surface of said front side and an inside surface of said back side and wherein said inside surface of said front side terminates at a peripheral edge and said inside surface of said back side terminates at a back edge, and wherein said back edge abuts said peripheral edge so as to form an included angle which is greater than about 100 degrees.

17. A method of attaching a tooth cap to a full-size real tooth, comprising the steps of:
provilding a generally hollow removable and re-usable tooth cap of the type that is attachable to and removable from a user's real tooth by the user, said tooth cap defining a cavity for receiving a full-size real tooth wherein the surface of said cavity is provided with surface features for enhancing the attachment of material for removably attaching said tooth cap to the full-size real tooth, said tooth cap having a front side and a back side which terminate at a distal end of said tooth cap, said cavity being defined by an inside surface of said front side and an inside surface of said backside, said backside of said tooth cap further defining a recessed path on its outer surface, said path extending longitudinally along said backside of said tooth cap from an area adjacent said distal end of said tooth cap to a back edge of said backside near a mid-section of the tooth cap at which said backside and said path terminate;

placing material for attaching said tooth cap to a full-size real tooth into said cavity of said tooth cap;

placing said tooth cap onto said full-size real tooth so that the attaching material envelops the surface features; and then biting down to adjust the tooth cap's position on the full-size real tooth so that interference caused by the tooth cap with the user's normal occlusion is minimized, while biting down, allowing the attaching material to set so that the tooth cap is affixed to the full-size real tooth in the position which minimizes said interference.

18. A method of attaching a tooth cap to a full-size real tooth, comprising the steps of:
providing a generally hollow removable and re-usable tooth cap of the type that is attachable to and removable from a user's real tooth by the user, said tooth cap defining a cavity for receiving a full-size real tooth as well as material for removably attaching said tooth cap to the full-size real tooth, said cavity having a bottom, and said tooth cap further defining a nonlinear passageway in the bottom of the tooth cap's cavity for receiving material to secure the material to the tooth cap, said nonlinear passageway extending from said bottom of said cavity to and through the outer surface of said tooth cap;

placing material for attaching said tooth cap to the full-size real tooth into the cavity of the tooth cap;

placing said tooth cap onto the full-size real tooth so that the attaching material flows into the tooth cap's nonlinear passageway; and then allowing the attaching material to set so that the attaching material is anchored to the tooth cap and the tooth cap is affixed to the full-size real tooth.

\* \* \* \* \*